(12) United States Patent
Hartman et al.

(10) Patent No.: US 7,005,267 B2
(45) Date of Patent: Feb. 28, 2006

(54) INTERNAL POSITIVE CONTROL FOR PROBE-BASED NUCLEIC ACID MOLECULE ASSAYS AND METHODS OF MAKING AND USING THEREOF

(75) Inventors: Laurie J. Hartman, Germantown, MD (US); David A. Norwood, Jr., Thurmont, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 263 days.

(21) Appl. No.: 10/376,323

(22) Filed: Mar. 3, 2003

(65) Prior Publication Data

US 2003/0211527 A1 Nov. 13, 2003

Related U.S. Application Data

(60) Provisional application No. 60/361,455, filed on Mar. 4, 2002.

(51) Int. Cl.
*C12Q 1/68* (2006.01)

(52) U.S. Cl. .......................................... 435/6; 435/91.1
(58) Field of Classification Search ..................... 435/6, 435/91.1, 91.2
See application file for complete search history.

(56) References Cited

U.S. PATENT DOCUMENTS

| | | | |
|---|---|---|---|
| 5,723,591 A | 3/1998 | Livak et al. | |
| 5,952,202 A | 9/1999 | Aoyagi et al. | |
| 6,312,930 B1 | 11/2001 | Tice, Jr. et al. | |

OTHER PUBLICATIONS

Notification of Transmittal of the International Search Report or the Declaration (Form PCT/ISA/220) issued for PCT/US03/06347.
International Search Report (Form PCT/ISA/210) issued for PCT/US03/06347.
Courtney, et al. (1999) "Development of Internal Controls for Probe–Based Nucleic Acid Diagnostic Assays" Anal. Biochem. 270(2):249–256.
Hartman, et al. (2005) "Development of a Novel Internal Positive Control for Taqman Based Assays" Mol. Cell. Probes 19:51–59.
Ho, et al. (1989) "Site–Directed Mutagenesis by Overlap Extension Using the Polymerase Chain Reaction" Gene 77(1):51–59.
Ursi, et al. (1998) "Construction of an Internal Control for the Detection of Chlamydia pneumoniae by PCR" Mol. Cell. Probes 12:235–238.
European Supplementary Search Report mailed Jul. 18, 2005.

*Primary Examiner*—Gary Benzion
(74) *Attorney, Agent, or Firm*—Elizabeth Arwine

(57) ABSTRACT

Disclosed herein are isolated nucleic acid molecules that may be used as an internal positive controls in probe-based nucleic acid assays such as TaqMan® based assays. Also disclosed are probes comprising the isolated nucleic acid molecule of the present invention. The probes may comprise a reporter molecule and a quencher molecule. Also disclosed are assays which comprise using the probe of the present invention. The probes may be used to distinguish false negative results from true negative results in assays for a target nucleic acid molecule. The probe may be used in conjunction with probe-based nucleic acid assays for the detection of an organism such as one belonging to *Bacillus, Mycobacterium, Francisella, Brucella, Clostridium, Yersinia, Variola, Orthopox,* or *Burkholderia*.

27 Claims, 2 Drawing Sheets

Figure 2

SEQUENCE LISTING

```
<160> NUMBER OF SEQ ID NOS: 88
<210> SEQ ID NO 1
<211> LENGTH: 153
<212> TYPE: DNA
<213> ORGANISM: Artificial Sequence
<220> FEATURE:
<223> OTHER INFORMATION: Description of Artificial Sequence: Bacillus
      anthracis Protective Antigen

<400> SEQUENCE: 1
ttcaagttgt actggaccga ttctcaaaat aaaaaagaag tgatttctag tgataactta      60
caattgccag aattaaaaca aaaatcttcg aactcaagaa aaaagcgaag tacaagtgct     120
ggacctacgg ttccagaccg tgacaatgat gga                                  153

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Upper
      Primer:IPC3L

<400> SEQUENCE: 2
cgttgttacc gactggatta ttac                                             24

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Lower
      Primer:IPC5U

<400> SEQUENCE: 3
tccgcatacc agttgttgtc g                                                21

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Probe:
      IPCP35F
```

```
<400> SEQUENCE: 4
cgtagttgat cgctctcagt ccatccgt                                          28

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Upper
      Primer:BAPA3U

<400> SEQUENCE: 5
ttcaagttgt actggaccga ttctc                                             25

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Lower
      Primer:BAPA5L

<400> SEQUENCE: 6
tccatcattg tcacggtctg g                                                 21

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence:Probe:
      BAPA3P2A

<400> SEQUENCE: 7
ccgtaggtcc agcacttgta cttcgctt                                          28

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: BANPAIS1

<400> SEQUENCE: 8
gtaacaatgt gggtagatga cc                                                22

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: PA35PC1L

<400> SEQUENCE: 9
tctcagtcca tccgtttttc ttgagttc                                          28

<210> SEQ ID NO 10
<211> LENGTH: 252
<212> TYPE: DNA
<213> ORGANISM: Artificial Sequence
<220> FEATURE:
<223> OTHER INFORMATION: Description of Artificial Sequence: Fragment 1

<400> SEQUENCE: 10
gtaacaatgt gggtagatga ccaagaagtg attaataaag cttctaattc taacaaaatc       60
```

```
agattagaaa aaggaagatt atatcaaata aaaattcaat atcaacgaga aaatcctact      120
gaaaaaggat tggatttcaa gttgtactgg accgattctc aaaataaaaa agaagtgatt      180
tctagtgata acttacaatt gccagaatta aaacaaaaat cttcgaactc aagaaaaacg      240
gatggactga ga                                                         252
```

```
<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: BANPAIA1

<400> SEQUENCE: 11
cttatcaatc cgtcctgtaa cc                                              22
```

```
<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: PA35PC1U

<400> SEQUENCE: 12
gcgatcaact acgttccaga ccgtg                                           25
```

```
<210> SEQ ID NO 13
<211> LENGTH: 225
<212> TYPE: DNA
<213> ORGANISM: Artificial Sequence
<220> FEATURE:
<223> OTHER INFORMATION: Description of Artificial Sequence: Fragment 2

<400> SEQUENCE: 13
gcgatcaact acgttccaga ccgtgacaat gatggaatcc ctgattcatt agaggtagaa      60
ggatatacgg ttgatgtcaa aaataaaaga acttttcttt caccatggat ttctaatatt     120
catgaaaaga aaggattaac caaatataaa tcatctcctg aaaaatggag cacggcttct     180
gatccgtaca gtgatttcga aaaggttaca ggacggattg ataag                    225
```

```
<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: BANPAIS1

<400> SEQUENCE: 14
gtaacaatgt gggtagatga cc                                              22
```

```
<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: PA35PC2L

<400> SEQUENCE: 15
cgtagttgat cgctctcagt ccatccgt                                        28
```

```
<210> SEQ ID NO 16
<211> LENGTH: 265
<212> TYPE: DNA
<213> ORGANISM: Artificial Sequence
```

```
<220> FEATURE:
<223> OTHER INFORMATION: Description of Artificial Sequence: Fragment 3

<400> SEQUENCE: 16
gtaacaatgt gggtagatga ccaagaagtg attaataaag cttctaattc taacaaaatc      60
agattagaaa aaggaagatt atatcaaata aaaattcaat atcaacgaga aaatcctact     120
gaaaaaggat tggatttcaa gttgtactgg accgattctc aaaataaaaa agaagtgatt     180
tctagtgata acttacaatt gccagaatta aaacaaaaat cttcgaactc aagaaaaacg     240
gatggactga gagcgatcaa ctacg                                          265

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: BANPAIA1

<400> SEQUENCE: 17
cttatcaatc cgtcctgtaa cc                                              22

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: PA35PC2U

<400> SEQUENCE: 18
acggatggac tgagagcgat caactacg                                        28

<210> SEQ ID NO 19
<211> LENGTH: 240
<212> TYPE: DNA
<213> ORGANISM: Artificial Sequence
<220> FEATURE:
<223> OTHER INFORMATION: Description of Artificial Sequence: Fragment 4

<400> SEQUENCE: 19
acggatggac tgagagcgat caactacgtt ccagaccgtg acaatgatgg aatccctgat      60
tcattagagg tagaaggata tacggttgat gtcaaaaata aaagaacttt tctttcacca     120
tggatttcta atattcatga aaagaaagga ttaaccaaat ataaatcatc tcctgaaaaa     180
tggagcacgg cttctgatcc gtacagtgat ttcgaaaagg ttacaggacg gattgataag     240

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: BANPABIS1

<400> SEQUENCE: 20
caacgagaaa atcctactga aaaag                                           25

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: BANPABIA1

<400> SEQUENCE: 21
```

-continued

```
gaaatcactg tacggatcag aagc                                              24
```

<210> SEQ ID NO 22
<211> LENGTH: 348
<212> TYPE: DNA
<213> ORGANISM: Artificial Sequence
<220> FEATURE:
<223> OTHER INFORMATION: Description of Artificial Sequence: Fragment 5

<400> SEQUENCE: 22

```
caacgagaaa atcctactga aaaggattg gatttcaagt tgtactggac cgattctcaa         60
aataaaaaag aagtgatttc tagtgataac ttacaattgc cagaattaaa acaaaaatct      120
tcgaactcaa gaaaacgga tggactgaga gcgatcaact acgttccaga ccgtgacaat       180
gatggaatcc ctgattcatt agaggtagaa ggatatacgg ttgatgtcaa aaataaaaga      240
acttttcttt caccatggat ttctaatatt catgaaaaga aggattaac caaatataaa        300
tcatctcctg aaaaatggag cacggcttct gatccgtaca gtgatttc                   348
```

<210> SEQ ID NO 23
<211> LENGTH: 521
<212> TYPE: DNA
<213> ORGANISM: Artificial Sequence
<220> FEATURE:
<223> OTHER INFORMATION: Description of Artificial Sequence: Clone 11

<400> SEQUENCE: 23

```
gaaacagcta tgaccatgat tacgccaagc ttggtaccga gctcggatcc actagtaacg       60
gccgccagtg tgctggaatt cggcttcaac gagaaaatcc tactgaaaaa ggattggatt     120
tcaagttgta ctggaccgat tctcaaaata aaaagaagt gatttctagt gataacttac      180
aattgccaga attaaaacaa aaatcttcga actcaagaaa acggatgga ctgagagcga      240
tcaactacgt tccagaccgt gacaatgatg gaatccctga ttcattagag gtagaaggat     300
atacggttga tgtcaaaaat aaaagaactt ttctttcacc atggatttct aatattcatg     360
aaaagaaagg attaaccaaa tataaatcat ctcccgaaaa atggagcacg gcttctgatc     420
cgtacagtga tttcaagccg aattctgcag atatccatca cactggcggc cgctcgagca     480
tgcatctaga gggcccaatt cgccctatag tgagtcgtat t                         521
```

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: MOD31L

<400> SEQUENCE: 24

```
tcggtaacaa cgatccaatc ctttt                                             25
```

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: PCR II FOR

<400> SEQUENCE: 25

```
caggaaacag ctatgacc                                                     18
```

<210> SEQ ID NO 26
<211> LENGTH: 134

<212> TYPE: DNA
<213> ORGANISM: Artificial Sequence
<220> FEATURE:
<223> OTHER INFORMATION: Description of Artificial Sequence: Fragment 6

<400> SEQUENCE: 26
caggaaacag ctatgaccat gattacgcca agcttggtac cgagctcgga tccactagta    60
acggccgcca gtgtgctgga attcggcttc aacgagaaaa tcctactgaa aaaggattgg   120
atcgttgtta ccga                                                     134

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: MOD31U

<400> SEQUENCE: 27
ctggattatt accaaaataa aaaag                                          25

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: PCR II REV

<400> SEQUENCE: 28
tgtaaaacga cggccagt                                                  18

<210> SEQ ID NO 29
<211> LENGTH: 415
<212> TYPE: DNA
<213> ORGANISM: Artificial Sequence
<220> FEATURE:
<223> OTHER INFORMATION: Description of Artificial Sequence: Fragment 7

<400> SEQUENCE: 29
ctggattatt accaaaataa aaagaagtg atttctagtg ataacttaca attgccagaa     60
ttaaaacaaa aatcttcgaa ctcaagaaaa acggatggac tgagagcgat caactacgtt   120
ccagaccgtg acaatgatgg aatccctgat tcattagagg tagaaggata tacgttgat   180 gtcaaaaata aagaactttt tctttcacca tggatttcta atattcatga aaagaaagga   240
ttaaccaaat ataaatcatc tcctgaaaaa tggagcacgg cttctgatcc gtacagtgat   300
ttcaagccga attctgcaga tatccatcac actggcggcc gctcgagcat gcatctagag   360
ggcccaattc gccctatagt gagtcgtatt acaattcact ggccgtcgtt ttaca         415

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: MOD32L

<400> SEQUENCE: 30
ggtaataatc cagtcggtaa caacg                                          25

<210> SEQ ID NO 31
<211> LENGTH: 18
<212> TYPE: DNA
<213> ORGANISM: Artificial Sequence
<220> FEATURE:

```
<223> OTHER INFORMATION: Description of Artificial Sequence: PCR II FOR

<400> SEQUENCE: 31
caggaaacag ctatgacc                                                    18

<210> SEQ ID NO 32
<211> LENGTH: 147
<212> TYPE: DNA
<213> ORGANISM: Artificial Sequence
<220> FEATURE:
<223> OTHER INFORMATION: Description of Artificial Sequence: Fragment 8

<400> SEQUENCE: 32
caggaaacag ctatgaccat gattacgcca agcttggtac cgagctcgga tccactagta     60
acggccgcca gtgtgctgga attcggcttc aacgagaaaa tcctactgaa aaaggattgg    120
atcgttgtta ccgactggat tattacc                                        147

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: MOD32U

<400> SEQUENCE: 33
cgttgttacc gactggatta ttacc                                           25

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: PCR II REV

<400> SEQUENCE: 34
tgtaaaacga cggccagt                                                   18

<210> SEQ ID NO 35
<211> LENGTH: 427
<212> TYPE: DNA
<213> ORGANISM: Artificial Sequence
<220> FEATURE:
<223> OTHER INFORMATION: Description of Artificial Sequence: Fragment 9

<400> SEQUENCE: 35
cgttgttacc gactggatta ttaccaaaat aaaaagaag tgatttctag tgataactta      60
caattgccag aattaaaaca aaaatcttcg aactcaagaa aaacggatgg actgagagcg    120
atcaactacg ttccagaccg tgacaatgat ggaatccctg attcattaga ggtagaagga    180
tatacggttg atgtcaaaaa taaaagaact tttctttcac catggatttc taatattcat    240
gaaaagaaag gattaaccaa atataaatca tctcctgaaa aatggagcac ggcttctgat    300
ccgtacagtg atttcaagcc gaattctgca gatatccatc acactggcgg ccgctcgagc    360
atgcatctag agggcccaat tcgccctata gtgagtcgta ttacaattca ctggccgtcg    420
tttttaca                                                             427

<210> SEQ ID NO 36
<211> LENGTH: 549
<212> TYPE: DNA
<213> ORGANISM: Artificial Sequence
<220> FEATURE:
<223> OTHER INFORMATION: Description of Artificial Sequence: Clone 7
```

```
<400> SEQUENCE: 36
caggaaacag ctatgaccat gattacgcca agcttggtac cgagctcgga tccactagta      60
acggccgcca gtgtgctgga attcggcttc aacgagaaaa tcctactgaa aaaggattgg     120
atcgttgtta ccgactggat tattaccaaa ataaaaaaga gtgatttctt agtgataact     180
tacaattgcc agaattaaaa caaaaatctt cgaactcaag aaaaacggat ggactgagag     240
cgatcaacta cgttccagac cgtgacaatg atggaatccc tgattcatta gaggtagaag     300
gatatacggt tgatgtcaaa ataaaaagaa cttttctttc accatggatt tctaatattc     360
atgaaaagaa aggattaacc aaatataaat catctcctga aaaatggagc acggcttctg     420
atccgtacag tgatttcaag ccgaattctg cagatatcca tcacactggc ggccgctcga     480
gcatgcatct agagggccca attcgcccta gtgagtcg tattacaatt cactggccgt       540
cgttttaca                                                             549

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: MOD51U

<400> SEQUENCE: 37
tggtatgcgg aatccctgat tcatt                                            25

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: PCR II FOR

<400> SEQUENCE: 38
caggaaacag ctatgacc                                                    18

<210> SEQ ID NO 39
<211> LENGTH: 262
<212> TYPE: DNA
<213> ORGANISM: Artificial Sequence
<220> FEATURE:
<223> OTHER INFORMATION: Description of Artificial Sequence: Fragment 10

<400> SEQUENCE: 39
caggaaacag ctatgaccat gattacgcca agcttggtac cgagctcgga tccactagta      60
acggccgcca gtgtgctgga attcggcttg aaatcactgt acggatcaga agccgtgctc     120 cattttcgg gagatgattt atatttggtt aatcctttct tttcatgaat attagaaatc      180
catggtgaaa gaaagttctt tttatttttg acatcaaccg tatatccttc tacctctaat     240
gaatcaggga ttccgcatac ca                                              262

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: MOD51L

<400> SEQUENCE: 40
gttgttgtcg aacgtagttg atcgc                                            25
```

```
<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: PCR II REV

<400> SEQUENCE: 41
tgtaaaacga cggccagt                                                    18

<210> SEQ ID NO 42
<211> LENGTH: 286
<212> TYPE: DNA
<213> ORGANISM: Artificial Sequence
<220> FEATURE:
<223> OTHER INFORMATION: Description of Artificial Sequence: Fragment 11

<400> SEQUENCE: 42
gttgttgtcg aacgtagttg atcgctctca gtccatccgt ttttcttgag ttcgaagatt      60
tttgttttaa ttctggcaat tgtaagttat cactagaaat cacttctttt ttattttggt    120
aataatccag tcgtaacaa cgatccaatc cttttcagt aggattttct cgttgaagcc      180
gaattctgca gatatccatc acactggcgg ccgctcgagc atgcatctag agggcccaat    240
tcgccctata gtgagcgtat tacaattcac tggccgtcgt tttaca                    286

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: MOD52U

<400> SEQUENCE: 43
cgacaacaac tggtatgcgg a                                                21

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: PCR II FOR

<400> SEQUENCE: 44
caggaaacag ctatgacc                                                    18

<210> SEQ ID NO 45
<211> LENGTH: 272
<212> TYPE: DNA
<213> ORGANISM: Artificial Sequence
<220> FEATURE:
<223> OTHER INFORMATION: Description of Artificial Sequence: Fragment 12

<400> SEQUENCE: 45
caggaaacag ctatgaccat gattacgcca agcttggtac cgagctcgga tccactagta     60
acggccgcca gtgtgctgga attcggcttg aaatcactgt acggatcaga agccgtgctc    120 cattttttcgg gagatgattt atatttggtt aatcctttct tttcatgaat attagaaatc   180
catggtgaaa gaaagttct tttatttttg acatcaaccg tatatccttc tacctctaat    240
gaatcaggga ttccgcatac cagttgttgt cg                                   272

<210> SEQ ID NO 46
<211> LENGTH: 21
```

<212> TYPE: DNA
<213> ORGANISM: Artificial Sequence
<220> FEATURE:
<223> OTHER INFORMATION: Description of Artificial Sequence: MOD52L

<400> SEQUENCE: 46
tccgcatacc agttgttgtc g                                        21

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: PCR II REV

<400> SEQUENCE: 47
tgtaaaacga cggccagt                                            18

<210> SEQ ID NO 48
<211> LENGTH: 297
<212> TYPE: DNA
<213> ORGANISM: Artificial Sequence
<220> FEATURE:
<223> OTHER INFORMATION: Description of Artificial Sequence: Fragment 13

<400> SEQUENCE: 48
tccgcatacc agttgttgtc gaacgtagtt gatcgctctc agtccatccg ttttcttga      60 gttcgaagat ttttgtttta attctggcaa ttgtaagtta tcactagaaa tcacttcttt    120
tttattttgg taataatcca gtcggtaaca acgatccaat ccttttttcag taggattttc   180 tcgttgaagc cgaattctgc agatatccat cacactggcg gccgctcgag catgcatcta    240
gagggcccaa ttcgccctat agtgagcgta ttacaattca ctggccgtcg ttttaca        297

<210> SEQ ID NO 49
<211> LENGTH: 548
<212> TYPE: DNA
<213> ORGANISM: Artificial Sequence
<220> FEATURE:
<223> OTHER INFORMATION: Description of Artificial Sequence: IPC nucleic
      acid molecule

<400> SEQUENCE: 49
caggaaacag ctatgaccat gattacgcca agcttggtac cgagctcgga tccactagta      60
acggccgcca gtgtgctgga attcggcttg aaatcactgt acggatcaga agccgtgctc    120 cattttttcgg gagatgattt atatttggtt aatcctttct tttcatgaat attagaaatc    180
catggtgaaa gaaagttct ttattttg acatcaaccg tatatccttc tacctctaat       240
gaatcaggga ttccgcatac cagttgttgt cgaacgtagt tgatcgctct cagtccatcc    300 gttttcttg agttcgaaga tttttgtttt aattctggca attgtaagtt atcactagaa     360
atcacttctt ttatttttg gtaataatcc agtcggtaac aacgatccaa tccttttca     420 gtaggatttt ctcgttgaag ccgaattctg cagatatcca tcacactggc ggccgctcga    480
gcatgcatct agagggccca attcgcccta gtgagcgt attacaattc actggccgtc     540
gttttaca                                                             548

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: BAPA3U

```
<400> SEQUENCE: 50
ttcaagttgt actggaccga ttctc                                    25

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: BAPA5L

<400> SEQUENCE: 51
tccatcattg tcacggtctg g                                        21

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: BAPA3P2A

<400> SEQUENCE: 52
ccgtaggtcc agcacttgta cttcgctt                                 28

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: BACAPBU2

<400> SEQUENCE: 53
gctgaccaat ctaagcctgc                                          20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: BACAPBL2

<400> SEQUENCE: 54
ggcaaaacat ccctagcaaa                                          20

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: BACAPBP2

<400> SEQUENCE: 55
ttgtaattat gaattgccgc cctgacc                                  27

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: BROMPF394

<400> SEQUENCE: 56
aacaaggcca agaccagcac c                                        21

<210> SEQ ID NO 57
```

```
<211> LENGTH: 20
<212> TYPE: DNA
<213> ORGANISM: Artificial Sequence
<220> FEATURE:
<223> OTHER INFORMATION: Description of Artificial Sequence: BROMPR474

<400> SEQUENCE: 57
ctggaagttc cagccagcaa                                                   20

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence: BROMP25-
      420S

<400> SEQUENCE: 58
cagcatcaag cctgacgatt ggaagg                                            26

<210> SEQ ID NO 59
<211> LENGTH: 27
<212> TYPE: DNA
<213> ORGANISM: Artificial Sequence
<220> FEATURE:
<223> OTHER INFORMATION: Description of Artificial Sequence: CBOTA4U

<400> SEQUENCE: 59
gatataggct ttataggatt tcatcag                                           27

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: CBOTA4L

<400> SEQUENCE: 60
cctttctccc catccatc                                                     18

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: CBOTA4P2A

<400> SEQUENCE: 61
tcccatgagc aacccaaagt cctact                                            26

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: YPPLA3U

<400> SEQUENCE: 62
ggtaccgtaa ttaacgctgg                                                   20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: YPPLA3L
```

```
<400> SEQUENCE: 63
gtctgagtac ctcctttgcc                                              20

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: YPPLAP3F

<400> SEQUENCE: 64
acctaatgcc aaagtctttg cgga                                         24

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: BACAPB4U

<400> SEQUENCE: 65
cagataatgc atcgcttgct ttag                                         24

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: BACAPB4L

<400> SEQUENCE: 66
ggatgagcat tcaacatacc acg                                          23

<210> SEQ ID NO 67
<211> LENGTH: 29
<212> TYPE: DNA
<213> ORGANISM: Artificial Sequence
<220> FEATURE:
<223> OTHER INFORMATION: Description of Artificial Sequence: BACAPBP1S

<400> SEQUENCE: 67
cagaggctct tgggattgat gaggaaaca                                    29

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: BAVRRA3U

<400> SEQUENCE: 68
aaatgtatga atcaaacgaa acgc                                         24

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: BAVRRA3L

<400> SEQUENCE: 69
cagggcttac agattgaacg                                              20

<210> SEQ ID NO 70
<211> LENGTH: 22
```

```
<212> TYPE: DNA
<213> ORGANISM: Artificial Sequence
<220> FEATURE:
<223> OTHER INFORMATION: Description of Artificial Sequence: BAVRRA3P1S

<400> SEQUENCE: 70
cggtgcagca actacagcag ca                                            22

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence: FTTULU1

<400> SEQUENCE: 71
cagcatacaa taataaccca caagg                                         25

<210> SEQ ID NO 72
<211> LENGTH: 25
<212> TYPE: DNA
<213> ORGANISM: Artificial Sequence
<220> FEATURE:
<223> OTHER INFORMATION: Description of Artificial Sequence: FTTULL1

<400> SEQUENCE: 72
tcagcatact tagtaattgg gaagc                                         25

<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence: FTTULP1F

<400> SEQUENCE: 73
ttacaatggc aggctccaga aggttc                                        26

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: YPPIMU1

<400> SEQUENCE: 74
agtggccttg cagaaaaaa                                                19

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: YPPIML1

<400> SEQUENCE: 75
gtaaactcgg tttgcttgaa g                                             21

<210> SEQ ID NO 76
<211> LENGTH: 25
<212> TYPE: DNA
<213> ORGANISM: Artificial Sequence
<220> FEATURE:
<223> OTHER INFORMATION: Description of Artificial Sequence: YPPIMP1R

<400> SEQUENCE: 76
```
tgtctgtttc ccatagatgc catga                                         25

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: OPSPF89

<400> SEQUENCE: 77
gatgatgcaa ctctatcatg ta                                            22

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: OPSR219

<400> SEQUENCE: 78
gtataattat caaaatacaa gacgtc                                        26

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Op-p143S

<400> SEQUENCE: 79
agtgcttggt ataaggag                                                 18

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: FOPAF708

<400> SEQUENCE: 80
ctggtttaac atggttctttt ggtg                                         24

<210> SEQ ID NO 81
<211> LENGTH: 27
<212> TYPE: DNA
<213> ORGANISM: Artificial Sequence
<220> FEATURE:
<223> OTHER INFORMATION: Description of Artificial Sequence: FOPAR846

<400> SEQUENCE: 81
ccagcaggta aaacatactt agactca                                       27

<210> SEQ ID NO 82
<211> LENGTH: 28
<212> TYPE: DNA
<213> ORGANISM: Artificial Sequence
<220> FEATURE:
<223> OTHER INFORMATION: Description of Artificial Sequence: FtFOPA765S

<400> SEQUENCE: 82
tccaggataa tggtgcgact acagctgc                                      28

<210> SEQ ID NO 83
<211> LENGTH: 20
<212> TYPE: DNA
<213> ORGANISM: Artificial Sequence -continued

```
<220> FEATURE:
<223> OTHER INFORMATION: Description of Artificial Sequence: J7R3U

<400> SEQUENCE: 83
catcattggc ggttgattta                                              20

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: J7R3L

<400> SEQUENCE: 84
tcatctggag aatccacaac a                                            21

<210> SEQ ID NO 85
<211> LENGTH: 26
<212> TYPE: DNA
<213> ORGANISM: Artificial Sequence
<220> FEATURE:
<223> OTHER INFORMATION: Description of Artificial Sequence: VARJ7R3p

<400> SEQUENCE: 85
caagacgtcg ggaccaatta ctaata                                       26

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: BPISO2F1

<400> SEQUENCE: 86
ctcgaggtgg agaatgccc                                               19

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: BPISO2R1

<400> SEQUENCE: 87
cgctcggaga tgttgacctt c                                            21

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: BMISO2PF3

<400> SEQUENCE: 88
tggccgaagc aatgctcgat atgg                                         24
```

INTERNAL POSITIVE CONTROL FOR PROBE-BASED NUCLEIC ACID MOLECULE ASSAYS AND METHODS OF MAKING AND USING THEREOF

CROSS REFERENCE TO RELATED APPLICATIONS

This application claims the benefit of U.S. Provisional Patent Application No. 60/361,455 filed Mar. 4, 2002, which names Laurie J. Hartman and David A. Norwood, Jr. as co-inventors and is herein incorporated by reference in its entirety.

ACKNOWLEDGMENT OF GOVERNMENT SUPPORT

Employees of the United States Army made this invention. The government has rights in the invention.

BACKGROUND OF THE INVENTION

1. Field of the Invention

The present invention generally relates to probes comprising a reporter molecule and a quencher molecule for use in nucleic acid assays. In particular, the present invention relates to a universal internal positive control that may be used in polymerase chain reaction (PCR) based assays.

2. Description of the Related Art

Reporter molecule and quencher molecule pairs have been incorporated onto oligonucleotide probes in order to monitor, detect, or measure biological events associated with the reporter molecule and quencher molecule being separated or brought within a minimum quenching distance of each other. For example, probes have been developed where the intensity of the reporter molecule fluorescence increases due to the separation of the reporter molecule from the quencher molecule. Probes have also been developed which lose their fluorescence because the quencher molecule is brought into proximity with the reporter molecule. Reporter molecule and quencher molecule pair probes have been used to monitor hybridization assays and nucleic acid amplification reactions, such as polymerase chain reactions (PCR), by monitoring either the appearance or disappearance of the signal generated by the reporter molecule. See WO 90/03446; European Patent Application No. 0 601 889 A2; Mergney, et al., (1994) Nucleic Acids Research 22(6): 920–928; and Arnheim and Erlich, (1992) Ann. Rev. Biochem. 61:131–156.

Various real time PCR amplification product assays are known in the art. See e.g. Holland et al. (1991) PNAS 88:7276–7280; and U.S. Pat. No. 5,210,015. One assay uses a probe having a fluorescence reporter molecule and quencher molecule pair that is cleaved apart during amplification thereby resulting in a detectable fluorescent molecule in a concentration that is proportional to the amount of double-stranded DNA. These assays are known as Taq-Man® based assays. TaqMan® based assays use an oligonucleotide probe having a reporter molecule and quencher molecule pair that specifically anneals to a region of a target polynucleotide "downstream", i.e. in the direction of extension of primer binding sites. The reporter molecule and quencher molecule are positioned on the probe sufficiently close to each other such that whenever the reporter molecule is excited, the energy of the excited state nonradiatively transfers to the quencher molecule where it either dissipates nonradiatively or is emitted at a different emission frequency than that of the reporter molecule.

During strand extension by a DNA polymerase, the probe anneals to the template where it is digested by the 5'→3' exonuclease activity of the polymerase. As a result of the probe being digested, the reporter molecule is effectively separated from the quencher molecule such that the quencher molecule is no longer close enough to the reporter molecule to quench the fluorescence of the reporter molecule. Thus, as more and more probes are digested during amplification, the number of reporter molecules in solution increases, thereby resulting in an increasing number of unquenched reporter molecules which produce a stronger and stronger fluorescent signal.

TaqMan® based assays require internal positive control reagents to help distinguish between samples that are identified as negative because the sample lacks the target sequence and samples that are identified as negative because the presence of a PCR inhibitor. A TaqMan® Exogenous Internal Positive Control kit is commercially available from Applied Biosystems (Foster City, Calif.) to distinguish true target negatives from PCR inhibition. The TaqMan® Exogenous Internal Positive Control kit distinguishes two types of negative results. A negative call for the target sequence and a positive call for the internal positive control (IPC) indicates that no target sequence is present and a negative call for the target sequence and a negative call for the IPC suggests PCR inhibition.

Unfortunately, the TaqMan® Exogenous Internal Positive Control kits allow little flexibility as the kits are made with only one fluorescent dye, VIC™ (Applied Biosystems, Foster City, Calif.), which cannot be used on all TaqMan® chemistry based instruments and the primers and probe in the kit are mixed together by the manufacturer and therefore cannot be completely optimized for use with any PCR amplification product assay.

Thus, a need exists for an internal positive control that may be used with a variety of PCR amplification product assays.

SUMMARY OF THE INVENTION

The present invention generally relates to a nucleic acid molecule that may be used as an internal positive control in probe-based nucleic acid assays.

In some embodiments, the present invention relates to an isolated nucleic acid molecule comprising the sequence set forth in SEQ ID NO: 49. In some embodiments, the nucleic acid molecule consists essentially of the sequence set forth in SEQ ID NO: 49. In some embodiments, the nucleic acid molecule consists of the sequence set forth in SEQ ID NO: 49.

In some embodiments, the present invention provides an isolated nucleic acid molecule that has a sequence identity of at least about 70% over the 548 bp region of SEQ ID NO: 49. In preferred embodiments, the sequence identity is at least about 80%, preferably at least about 90%, more preferably at least about 95%.

In some embodiments, the present invention provides a probe comprising an isolated nucleic acid molecule of the present invention and a label.

In some embodiments, the present invention provides a probe comprising an isolated nucleic acid molecule of the present invention, a reporter molecule, and a quencher molecule. In preferred embodiments, the reporter molecule produces a signal upon the separation of the reporter mol ecule and the quencher molecule. In preferred embodiments, the quencher molecule is capable of quenching the signal of the reporter molecule. In some embodiments, the reporter molecule is a fluorophore such as FAM, ROX, Texas Red, TET, TAMRA, JOE, HEX, CAL Red, and VIC, preferably the fluorophore is FAM, ROX, or Texas Red. In some embodiments, the probe is capable of being cleaved by a protein thereby separating the reporter molecule from the quencher molecule. In preferred embodiments, the protein is Taq polymerase.

In some embodiments, the present invention provides an assay which comprises using a probe of the present invention. In preferred embodiments, the assay is a nucleic acid hybridization assay such as a TaqMan® based assay. In some embodiments, the assay further comprises conducting PCR amplification. The assay may further comprise detecting the presence or measuring the amount of the probe and detecting the presence or measuring the amount of a target nucleic acid molecule. In preferred embodiments of the present invention, the absence of the target nucleic acid molecule and the absence of the probe indicate a true negative result for the target nucleic acid molecule and the absence of the target nucleic acid molecule and the presence of the probe indicate a false negative result for the target nucleic acid molecule.

In some embodiments, the present invention provides a kit for a probe-based nucleic acid assay comprising an isolated nucleic acid molecule of the present invention packaged with instructions for use. In preferred embodiments, the isolated nucleic acid molecule contains a label such as a reporter molecule and a quencher molecule. In some embodiments, the probe-based nucleic acid assay is for the detection of an organism such as one belonging to *Bacillus, Mycobacterium, Francisella, Brucella, Clostridium, Yersinia, Variola, Orthopox,* or *Burkholderia.* The kit of the present invention may, further include reagents or components for detecting the presence of a nucleic acid molecule belonging to the organism.

In some embodiments, the present invention also provides a method of making an internal positive control nucleic acid molecule for a probe-based nucleic acid molecule assay which comprises creating a first DNA fragment and a second DNA fragment from a template DNA and first set of primers and a second set of primers; creating a third DNA fragment and a fourth DNA fragment from the first DNA fragment and the second DNA fragment with a third set of primers and a second set of primers; hybridizing the third DNA fragment and the fourth DNA fragment to obtain a first hybridized DNA; using a fifth primer set to create a fifth DNA fragment from the first hybridized DNA; using a sixth primer set and a seventh primer set to create a sixth DNA fragment and a seventh DNA fragment from the fifth DNA fragment; creating a eighth DNA fragment and a ninth DNA fragment from the sixth DNA fragment and the seventh DNA fragment using a eighth primer set and a ninth primer set; hybridizing the eighth DNA fragment and the ninth DNA fragment to obtain a second hybridized DNA; creating a tenth DNA fragment and an eleventh DNA fragment from the second hybridized DNA using a tenth set of primers and an eleventh set of primers; creating a twelfth DNA fragment and a thirteenth DNA fragment from the tenth DNA fragment and the eleventh DNA fragment using a twelfth set of primers and a thirteenth set of primers; hybridizing the twelfth DNA fragment and the thirteenth DNA fragment to obtain the internal positive control nucleic acid molecule. In some preferred embodiments, the method of making an internal positive control nucleic acid molecule for a probe-based nucleic acid molecule assay, wherein the internal positive control nucleic acid molecule contains a sequence that has a sequence identity of at least about 70% over the 548 bp region of SEQ ID NO: 49. In preferred embodiments, the sequence identity is at least about 80%, preferably at least about 90%, more preferably at least about 95%.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 2 schematically shows the site-directed mutagenesis process used to generate the IPC nucleic acid molecule of the present invention.

DETAILED DESCRIPTION OF THE INVENTION

Figure 1:
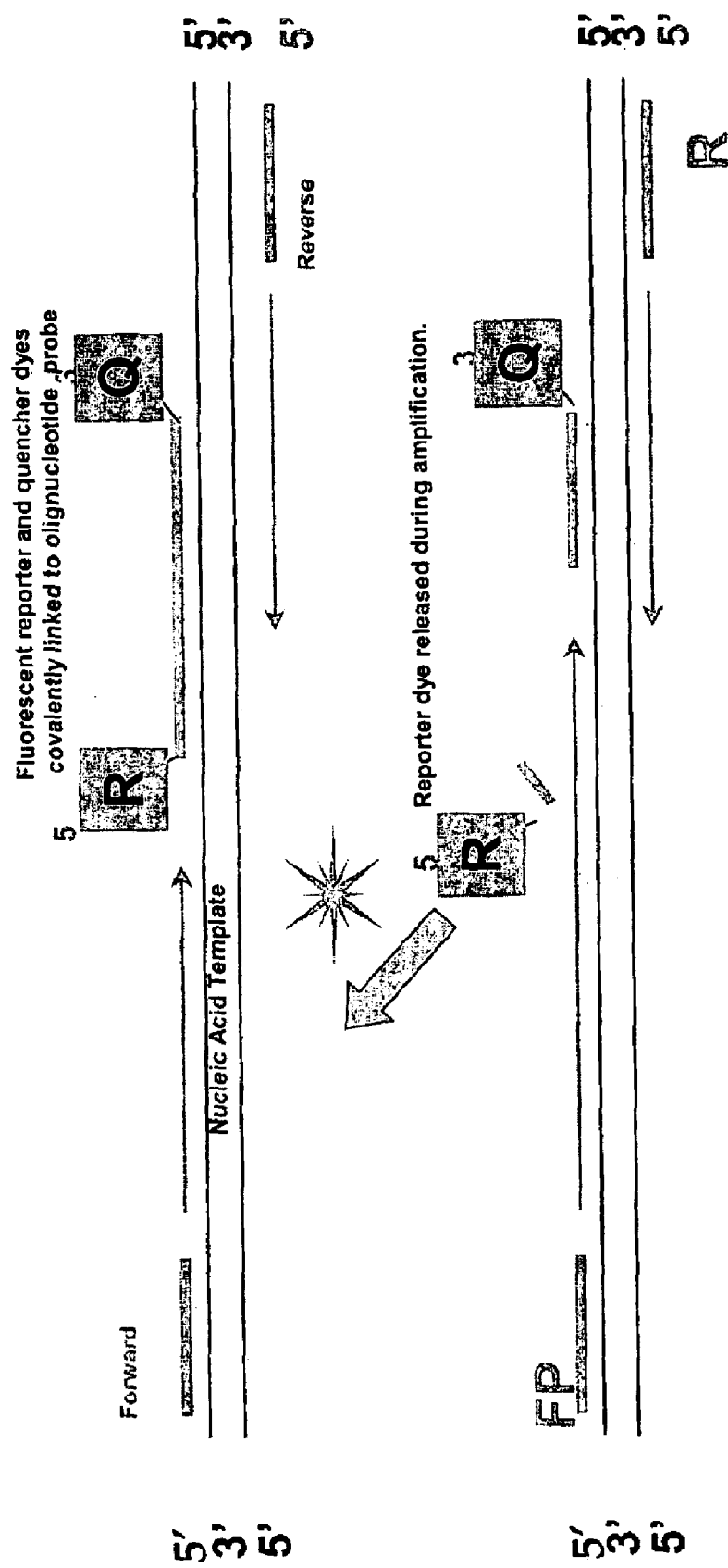
FIG. 1 is a schematic showing an example of a TaqMan® based assay.

The present invention provides an internal positive control (IPC) for use in nucleic acid hybridization assays, preferably probe-based nucleic acid assays such as TaqMan® based assays. An example of a TaqMan® based assay is schematically shown in FIG. 1. In particular, the present invention provides an oligonucleotide (IPC oligonucleotide) having a reporter molecule and a quencher molecule. The IPC oligonucleotide specifically anneals between the forward and reverse primers of a target sequence. The IPC oligonucleotide is cleaved by the 5' nuclease activity of Taq polymerase during PCR amplification and the reporter molecule is then separated from the quencher molecule to generate a sequence specific signal. With each amplification cycle, additional reporter molecules are separated from the quencher molecules. The intensity of a signal, such as fluorescence, may be monitored before, during, or after PCR amplification or a combination thereof.

The IPC nucleic acid molecule of the present invention may be used to distinguish a true negative result from a false negative result. As used herein, a "true negative" result correctly indicates that a sample lacks a target nucleic acid sequence. A "false negative" result incorrectly indicates the absence of a target nucleic acid sequence which may result from PCR inhibitors present in the sample or technical error.

The IPC nucleic acid molecule of the present invention may be used as a universal internal control as it comprises unique primer and probe sites and does not exhibit homology with any known nucleic acid sequences that may interfere with this assay, i.e. does not anneal with known nucleic acid sequences during conventional PCR techniques.

The IPC nucleic acid molecule of the present invention provides greater flexibility over commercially available IPCs as a variety of reporter molecule and quencher molecule pairs may be used and since the primers and IPC nucleic acid molecule sequences are independent, various concentrations of each may be used.

As described herein, the 153 base pair (bp) product from a *Bacillus anthracis* Protective Antigen (PA) PCR assay developed by the Diagnostic Systems Division (DSD) at the United States Army Medical Research Institute of Infectious Diseases (USAMRIID) was used (publication in progress). The 153 bp sequence is:

(SEQ ID NO:1)
5' TTCAAGTTGT ACTGGACCGA TTCTCAAAAT AAAAAAGAAG

TGATTTCTAG TGATAACTTA CAATTGCCAG AATTAAAACA

AAAATCTTCG AACTCAAGAA AAAAGCGAAG TACAAGTGCT

GGACCTACGG TTCCAGACCG TGACAATGAT GGA 3'.

The probe and both primer sites were mutated to predetermined sequences as follows:

Upper Primer: IPC3L
(SEQ ID NO:2)
5' CGT TGT TAC CGA CTG GAT TAT TAC C 3';

Lower Primer: IPC5U
(SEQ ID NO:3)
5' TCC GCA TAC CAG TTG TTG TCG 3'; and

Probe: IPCP35F
(SEQ ID NO:4)
5' CGT AGT TGA TCG CTC TCA GTC CAT CCG T 3'.

The original sequences were randomized and the random sequences were checked with a nucleotide BLAST search to confirm their uniqueness. The original sequences of the PA assay were as follows:

Upper Primer: BAPA3U
(SEQ ID NO:5)
5' TTC AAG TTG TAC TGG ACC GAT TCT C 3';

Lower Primer: BAPA5L
(SEQ ID NO:6)
5' tcc atc att gtc acg gtc tgg 3'; and

Probe: BAPA3P2A
(SEQ ID NO:7)
5' CCG TAG TCA GCA CAC TTG TAC TTC GCT T 3'.

The probe site was mutated first, followed by the upper primer site and then finally the lower primer site. As disclosed in Example 1, the mutations were conducted with PCR-based site directed mutagenesis methods known in the art. See Courtney, B. C., et al. (1999) Analytical Biochemistry 270:249–256. The methods were the same for all three sites, the only differences were the mutagenic oligonucleotide sequences.

Generally, mutations of each site were performed in three stages comprising five steps. For the initial probe mutation, genomic *Bacillus anthracis* DNA was used, and for the subsequent primer mutations, the plasmid DNA from the clone of the previous mutation was used. Mutagenic oligonucleotides were used to introduce the desired mutations. For round 1, these oligos contained ½ the sequence of *B. anthracis* genomic DNA and ½ the sequence of the desired mutation. These mutagenic oligos were paired up with an oligo outside of the final 153 bp PA product. When amplified with PCR, the result was two products each containing half of the final desired mutation sequence. For round 2, these mutagenic oligos consisted of ½ the new sequence that was introduced in round 1 and ½ the sequence of the rest of the desired mutation. The two products from round 1 were used as templates. Again, these mutagenic oligos were paired up with an oligo outside of the final 153 bp PA product. When amplified with PCR, the result was two products each containing all of the final desired mutation sequence. Finally in round 3, the two products from round 2 were used as primers on each other and ligated together, in addition the two oligos outside of the 153 bp product were used to further amplify it and increase the copy number of the final product. This final product was ligated into the pCR2.1 vector (Invitrogen Corporation, Carlsbad, Calif.) and transformed into competent INVαF' *E. coli* (Invitrogen Corporation, Carlsbad, Calif.).

For round 1 of the probe mutation, the template DNA used was 1 ng of Ames genomic DNA (USAMRIID, Ft. Detrick, Md.), and the primers were:

BANPAIS1
5' GTA ACA ATG TGG GTA GAT GAC C 3'    (SEQ ID NO:8)

PA35PC1L
(SEQ ID NO:9)
5' TCT CAG TCC ATC CGT TTT TCT TGA GTT C 3'

The product, Fragment 1, was a 252 bp product as follows:

(SEQ ID NO:10)
5'GTAACAATGTGGGTAGATGACCAAGAAGTGATTAATAAAGCTTCTAAT

TCTAACAAAATCAGATTAGAAAAAGGAAGATTATATCAAATAAAAATTCA

ATATCAACGAGAAAATCCTACTGAAAAAGGATTGGATTTCAAGTTGTACT

GGACCGATTCTCAAAATAAAAAAGAAGTGATTTCTAGTGATAACTTACAA

TTGCCAGAATTAAAACAAAAATCTTCGAACTCAAGAAAAACGGATGGACT

GAGA 3'.

Also for round 1 of the probe mutation, the template DNA used was 1 ng of Ames genomic DNA (USAMRIID, Ft. Detrick, Md.), and the primers were:

BANPAIA1
5' CTT ATC AAT CCG TCC TGT AAC C 3'    (SEQ ID NO:11)

PA35PC1U
(SEQ ID NO:12)
5' GCG ATC AAC TAC GTT CCA GAC CGT G 3'

The product, Fragment 2, was a 225 bp product as follows:

(SEQ ID NO:13)
5'GCGATCAACTACGTTCCAGACCGTGACAATGATGGAATCCCTGATTCA

TTAGAGGTAGAAGGATATACGGTTGATGTCAAAAATAAAAGAACTTTTCT

TTCACCATGGATTTCTAATATTCATGAAAAGAAAGGATTAACCAAATATA

AATCATCTCCTGAAAAATGGAGCACGGCTTCTGATCCGTACAGTGATTTC

GAAAAGGTTACAGGACGGATTGATAAG 3'.

Both Fragment 1 and Fragment 2 were purified with the QIAquick PCR Purification Kit (Qiagen, Valencia, Calif.).

For round 2 of the probe mutation, the template DNA used was Fragment 1, the 252 bp product from BANPAIS1/PA35PC1L, and the primers used were:

BANPAIS1
5' GTA ACA ATG TGG GTA GAT GAC C 3'    (SEQ ID NO:14)

PA35PC2L
                                        (SEQ ID NO:15)
5' CGT AGT TGA TCG CTC TCA GTC CAT CCG T 3'

The product, Fragment 3, was a 265 bp product as follows:

(SEQ ID NO:16)
5'GTAACAATGTGGGTAGATGACCAAGAAGTGATTAATAAAGCTTCTAAT

TCTAACAAAATCAGATTAGAAAAAGGAAGATTATATCAAATAAAAATTCA

ATATCAACGAGAAAATCCTACTGAAAAAGGATTGGATTTCAAGTTGTACT

GGACCGATTCTCAAAATAAAAAAGAAGTGATTTCTAGTGATAACTTACAA

TTGCCAGAATTAAAACAAAAATCTTCGAACTCAAGAAAAACGGATGGACT

GAGAGCGATCAACTACG 3'.

Also for round 2 of the probe mutation, the template DNA used was Fragment 2, the 225 bp product from BANPAIA1/PA35PC2U, and the primers used were:

BANPAIA1
5' CTT ATC AAT CCG TCC TGT AAC C 3'    (SEQ ID NO:17)

PA35PC2U
                                        (SEQ ID NO:18)
5' ACG GAT GGA CTG AGA GCG ATC AAC TAC C 3'

The product, Fragment 4, was a 240 bp product as follows:

(SEQ ID NO:19)
5'ACGGATGGACTGAGAGCGATCAACTACGTTCCAGACCGTGACAATGAT

GGAATCCCTGATTCATTAGAGGTAGAAGGATATACGGTTGATGTCAAAAA

TAAAAGAACTTTTCTTTCACCATGGATTTCTAATATTCATGAAAAGAAAG

GATTAACCAAATATAAATCATCTCCTGAAAAATGGAGCACGGCTTCTGAT

CCGTACAGTGATTTCGAAAAGGTTACAGGACGGATTGATAAG 3'

Both Fragment 3 and Fragment 4 were purified with the QIAquick PCR Purification Kit (Qiagen, Valencia, Calif.).

For round 3, Fragment 3 (265 bp product from BANPAIS1/PA35PC2L) was hybridized with Fragment 4 (240 bp product from BANPAIA1/PA35PC2U). An additional 1 µM each of BANPAIS1 and BANPAIA1 primers were added to create more product. A new primer set that was inside BANPAIS1/BANPAIA1, but still outside BAPA3U/BAPA5L was developed. The primers set is as follows:

BANPABIS1
                                        (SEQ ID NO:20)
5' CAA CGA GAA AAT CCT ACT GAA AAA G 3'

BANPABIA1
                                        (SEQ ID NO:21)
5' GAA ATC ACT GTA CGG ATC AGA AGC 3'

Round 3 was repeated with the addition of the new primer set. The product, Fragment 5, was 348 bp product and is as follows:

(SEQ ID NO:22)
5'CAACGAGAAAATCCTACTGAAAAAGGATTGGATTTCAAGTTGTACTGG

ACCGATTCTCAAAATAAAAAAGAAGTGATTTCTAGTGATAACTTACAATT

GCCAGAATTAAAACAAAAATCTTCGAACTCAAGAAAAACGGATGGACTGA

GAGCGATCAACTACGTTCCAGACCGTGACAATGATGGAATCCCTGATTCA

TTAGAGGTAGAAGGATATACGGTTGATGTCAAAAATAAAAGAACTTTTCT

TTCACCATGGATTTCTAATATTCATGAAAAGAAAGGATTAACCAAATATA

AATCATCTCCTGAAAAATGGAGCACGGCTTCTGATCCGTACAGTGATTT

C 3'.

Fragment 5 was gel purified with the QIAquick Gel Extraction Kit and cloned using the Original TA Cloning Kit (Invitrogen Corporation, Carlsbad, Calif.). All of the clones were sequenced with both forward and reverse primers in duplicate. Clone 11 was chosen because it had the exact mutated sequence that we were trying to achieve and the rest of the sequence remained unaltered. The Qiagen Plasmid Mini Purification Kit (Qiagen, Carlsbad, Calif.) was used to purify the plasmid DNA for further mutations.

For round 1 of the upper primer mutation, the template DNA used was 1 ng of purified plasma DNA from Clone 11 having the following sequence:

(SEQ ID NO:23)
5'GAAACAGCTATGACCATGATTACGCCAAGCTTGGTACCGAGCTCGGAT

CCACTAGTAACGGCCGCCAGTGTGCTGGAATTCGGCTTCAACGAGAAAAT

CCTACTGAAAAAGGATTGGATTTCAAGTTGTACTGGACCGATTCTCAAAA

TAAAAAAGAAGTGATTTCTAGTGATAACTTACAATTGCCAGAATTAAAAC

AAAAATCTTCGAACTCAAGAAAAACGGATGGACTGAGAGCGATCAACTAC

GTTCCAGACCGTGACAATGATGGAATCCCTGATTCATTAGAGGTAGAAGG

ATATACGGTTGATGTCAAAAATAAAAGAACTTTTCTTTCACCATGGATTT

CTAATATTCATGAAAAGAAAGGATTAACCAAATATAAATCATCTCCCGAA

AAATGGAGCACGGCTTCTGATCCGTACAGTGATTTCAAGCCGAATTCTGC

AGATATCCATCACACTGGCGGCCGCTCGAGCATGCATCTAGAGGGCCCAA

TTCGCCCTATAGTGAGTCGTATT 3'.

The primers used were as follows:

MOD31L
                                        (SEQ TD NO:24)
5' TCG GTA ACA ACG ATC CAA TCC TTT T 3'.

PCR II FOR
5' CAG GAA ACA GCT ATG ACC 3'.          (SEQ ID NO:25)

The product, Fragment 6, was a 134 bp product as follows:

(SEQ ID NO:26)
5'CAGGAAACAGCTATGACCATGATTACGCCAAGCTTGGTACCGAGCTCG

GATCCACTAGTAACGGCCGCCAGTGTGCTGGAATTCGGCTTCAACGAGAA

AATCCTACTGAAAAGGATTGGATCGTTGTTACCGA 3'.

Also for round 1 of the upper primer mutation, the template DNA used was 1 ng of purified plasma DNA from Clone 11 and the primers used were as follows:

MOD31U
(SEQ ID NO:27)
5' CTG GAT TAT TAC CAA AAT AAA AAA G 3'.

PCR II REV
5' TGT AAA ACG ACG GCC AGT 3'. (SEQ ID NO:28)

The product, Fragment 7, was a 415 bp product as follows:

(SEQ ID NO:29)
5'CTGGATTATTACCAAAATAAAAAAGAAGTGATTTCTAGTGATAACTTA

CAATTGCCAGAATTAAAACAAAAATCTTCGAACTCAAGAAAAACGGATGG

ACTGAGAGCGATCAACTACGTTCCAGACCGTGACAATGATGGAATCCCTG

ATTCATTAGAGGTAGAAGGATATACGGTTGATGTCAAAAATAAAAGAACT

TTTCTTTCACCATGGATTTCTAATATTCATGAAAAGAAAGGATTAACCAA

ATATAAATCATCTCCTGAAAAATGGAGCACGGCTTCTGATCCGTACAGTG

ATTTCAAGCCGAATTCTGCAGATATCCATCACACTGGCGGCCGCTCGAGC

ATGCATCTAGAGGGCCCAATTCGCCCTATAGTGAGTCGTATTACAATTCA

CTGGCCGTCGTTTTACA 3'.

Fragment 6 and Fragment 7 were purified with the QIAquick PCR Purification Kit (Qiagen, Valencia, Calif.).

For round 2 of the upper primer mutation, the template used was Fragment 6, the 134 bp product from MOD31L/ PCR II FOR, and the primers used were as follows:

MOD32L
(SEQ ID NO:30)
5' GGT AAT AAT CCA GTC GGT AAC AAC G 3'.

PCR II FOR
5' CAG GAA ACA GCT ATG ACC 3'. (SEQ ID NO:31)

The product, Fragment 8, is a 147 bp product as follows:

(SEQ ID NO:32)
5'CAGGAAACAGCTATGACCATGATTACGCCAAGCTTGGTACCGAGCTC

GGATCCACTAGTAACGGCCGCCAGTGTGCTGGAATTCGGCTTCAACGAG

AAAATCCTACTGAAAAAGGATTGGATCGTTGTTACCGACTGGATTATTA

CC 3'.

Also for round 2 of the upper primer mutation, the template used was Fragment 7, the 415 bp product from MOD31U/PCR II REV, and the primers used were as follows:

MOD32U
(SEQ ID NO:33)
5' CGT TGT TAC CGA CTG GAT TAT TAC C 3'.

PCR II REV
5' TGT AAA ACG ACG GCC AGT 3'. (SEQ ID NO:34)

The product, Fragment 9, was a 427 bp product as follows:

(SEQ ID NO:35)
5'CGTTGTTACCGACTGGATTATTACCAAAATAAAAAAGAAGTGATTTCT

AGTGATAACTTACAATTGCCAGAATTAAAACAAAAATCTTCGAACTCAAG

AAAAACGGATGGACTGAGAGCGATCAACTACGTTCCAGACCGTGACAATG

ATGGAATCCCTGATTCATTAGAGGTAGAAGGATATACGGTTGATGTCAAA

AATAAAAGAACTTTTCTTTCACCATGGATTTCTAATATTCATGAAAAGAA

AGGATTAACCAAATATAAATCATCTCCTGAAAAATGGAGCACGGCTTCTG

ATCCGTACAGTGATTTCAAGCCGAATTCTGCAGATATCCATCACACTGGC

GGCCGCTCGAGCATGCATCTAGAGGGCCCAATTCGCCCTATAGTGAGTCG

TATTACAATTCACTGGCCGTCGTTTTACA 3'.

Fragment 8 and Fragment 9 were purified with the QIAquick Gel Extraction Kit (Qiagen, Valencia, Calif.).

For round 3, Fragment 8 and Fragment 9 were hybridized. Additional PCR II FOR and PCR II: REV primers were added. The product was 549 bp as follows:

(SEQ ID NO:36)
5'CAGGAAACAGCTATGACCATGATTACGCCAAGCTTGGTACCGAGCTCG

GATCCACTAGTAACGGCCGCCAGTGTGCTGGAATTCGGCTTCAACGAGAA

AATCCTACTGAAAAAGGATTGGATCGTTGTTACCGACTGGATTATTACCA

AAATAAAAAGAAGTGATTTCTAGTGATAACTTACAATTGCCAGAATTAA

AACAAAAATCTTCGAACTCAAGAAAAACGGATGGACTGAGAGCGATCAAC

TACGTTCCAGACCGTGACAATGATGGAATCCCTGATTCATTAGAGGTAGA

AGGATATACGGTTGATGTCAAAAATAAAAGAACTTTTCTTTCACCATGGA

TTTCTAATATTCATGAAAAGAAAGGATTAACCAAATATAAATCATCTCCT

GAAAAATGGAGCACGGCTTCTGATCCGTACAGTGATTTCAAGCCGAATTC

TGCAGATATCCATCACACTGGCGGCCGCTCGAGCATGCATCTAGAGGGCC

CAATTCGCCCTATAGTGAGTCGTATTACAATTCACTGGCCGTCGTTTTAC

A 3'.

The product was gel purified with the QIAquick Gel Extraction Kit and cloned using the Original TA Cloning Kit (Invitrogen Corp., Carlsbad, Calif.). All of the clones were sequenced with both forward and reverse primers in duplicate. Clone 7 was selected because it had the exact mutation sequence that we were trying to achieve, and the rest of the sequence remained unaltered. The plasmid DNA was purified using a Qiagen Plasmid Mini Purification Kit (Qiagen, Carlsbad, Calif.).

For round 1 of the lower primer mutation, the template DNA used was 1 ng of the purified plasmid DNA from clone 7. The primers used were as follows:

MOD51U
(SEQ ID NO:37)
5' TGG TAT GCG AAT TCC CTG ATT CAT T 3'

PCR II FOR
5' CAG GAA ACA GCT ATG ACC 3' (SEQ ID NO:38)

The product, Fragment 10, was a 262 bp product as follows:

(SEQ ID NO:39)
5'CAGGAAACAGCTATGACCATGATTACGCCAAGCTTGGTACCGAGCTCG

GATCCACTAGTAACGGCCGCCAGTGTGCTGGAATTCGGCTTGAAATCACT

GTACGGATCAGAAGCCGTGCTCCATTTTTCGGGAGATGATTTATATTTGG

TTAATCCTTTCTTTTCATGAATATTAGAAATCCATGGTGAAAGAAAAGTT

CTTTTATTTTTGACATCAACCGTATATCCTTCTACCTCTAATGAATCAGG

GATTCCGCATACCA 3'.

Also for round 1 of the lower primer mutation, the template used was 1 ng of the purified plasmid DNA from clone 7, and the primers used were as follows:

MOD51L
(SEQ ID NO:40)
5' GTT GTT GTC GAA CGT AGT TGA TCG C 3'

PCR II REV
5' TGT AAA ACG ACG GCC AGT 3'     (SEQ ID NO:41)

The product, Fragment 11, was a 286 bp product as follows:

(SEQ ID NO:42)
5'GTTGTTGTCGAACGTAGTTGATCGCTCTCAGTCCATCCGTTTTTCTTG

AGTTCGAAGATTTTTGTTTTAATTCTGGCAATTGTAAGTTATCACTAGAA

ATCACTTCTTTTTTATTTTGGTAATAATCCAGTCGGTAACAACGATCCAA

TCCTTTTTCAGTAGGATTTTCTCGTTGAAGCCGAATTCTGCAGATATCCA

TCACACTGGCGGCCGCTCGAGCATGCATCTAGAGGGCCCAATTCGCCCTA

TAGTGAGCGTATTACAATTCACTGGCCGTCGTTTTACA 3'.

Fragment 10 and Fragment 11, were purified using a QIAquick PCR Purification Kit (Qiagen, Valencia, Calif.).

For round 2 of the lower primer mutation, the template used was Fragment 10, the 262 bp product from MOD51U/PCR II FOR. The primers used were as follows:

MOD52U
5' CGA CAA CAA CTG GTA TGC GGA 3'     (SEQ ID NO:43)

PCR II FOR
5' CAG GAA ACA GCT ATG ACC 3'     (SEQ ID NO:44)

The product, Fragment 12, was a 272 bp product as follows:

(SEQ ID NO:45)
5'CAGGAAACAGCTATGACCATGATTACGCCAAGCTTGGTACCGAGCTCG

GATCCACTAGTAACGGCCGCCAGTGTGCTGGAATTCGGCTTGAAATCACT

GTACGGATCAGAAGCCGTGCTCCATTTTTCGGGAGATGATTTATATTTGG

TTAATCCTTTCTTTTCATGAATATTAGAAATCCATGGTGAAAGAAAGTTC

TTTTATTTTTGACATCAACCGTATATCCTTCTACCTCTAATGAATCAGGG

ATTCCGCATACCAGTTGTTGTCG 3'.

Also for round 2 of the lower primer mutation, the template used was Fragment 11, the 286 bp product from MOD51L/PCR II REV. The primers used were as follows:

MOD52L
5' TCCGCATACCAGTTGTTGTCG 3'     (SEQ ID NO:46)

PCR II REV
5' TGTAAAACGACGGCCAGT 3'     (SEQ ID NO:47)

The product, Fragment 13, was a 296 bp product as follows:

(SEQ ID NO:48)
5'TCCGCATACCAGTTGTTGTCGAACGTAGTTGATCGCTCTCAGTCCAT

CCGTTTTTCTTGAGTTCGAAGATTTTTGTTTTAATTCTGGCAATTGTAA

GTTATCACTAGAAATCACTTCTTTTTTATTTTGGTAATAATCCAGTCGG

TAACAACGATCCAATCCTTTTTCAGTAGGATTTTCTCGTTGAAGCCGAA

TTCTGCAGATATCCATCACACTGGCGGCCGCTCGAGCATGCATCTAGAG

GGCCCAATTCGCCCTATAGTGAGCGTATTACAATTCACTGGCCGTCGTT

TTACA 3'.

Fragment 12 and Fragment 13 were purified with the QIAquick PCR Purification Kit (Qiagen, Valencia, Calif.).

For round 3 of the lower primer mutation, Fragment 12 was hybridized with Fragment 13. Additional PCR II FOR and PCR II REV primers were added. The product was 548 bp as follows:

(SEQ ID NO:49)
5'CAGGAAACAGCTATGACCATGATTACGCCAAGCTTGGTACCGAGCTCG

GATCCACTAGTAACGGCCGCCAGTGTGCTGGAATTCGGCTTGAAATCACT

GTACGGATCAGAAGCCGTGCTCCATTTTTCGGGAGATGATTTATATTTGG

TTAATCCTTTCTTTTCATGAATATTAGAAATCCATGGTGAAAGAAAAGTT

CTTTTATTTTTGACATCAACCGTATATCCTTCTACCTCTAATGAATCAGG

GATTCCGCATACCAGTTGTTGTCGAACGTAGTTGATCGCTCTCAGTCCAT

CCGTTTTTCTTGAGTTCGAAGATTTTTGTTTTAATTCTGGCAATTGTAAG

TTATCACTAGAAATCACTTCTTTTTTATTTTGGTAATAATCCAGTCGGTA

ACAACGATCCAATCCTTTTTCAGTAGGATTTTCTCGTTGAAGCCGAATTC

TGCAGATATCCATCACACTGGCGGCCGCTCGAGCATGCATCTAGAGGGCC

CAATTCGCCCTATAGTGAGCGTATTACAATTCACTGGCCGTCGTTTTAC

A 3'.

The product was gel purified with the QIAquick Gel Extraction Kit and cloned using the Original TA Cloning Kit (Invitrogen Corporation, Carlsbad, Calif.). All of the clones were sequenced with both forward and reverse primers in duplicate. Clone 1 was selected because it had the mutated sequence of the 548 bp product (SEQ ID NO: 49) and the rest of the sequence remained unaltered. The Qiagen Plasmid Mini Purification Kit (Qiagen, Carlsbad, Calif.) was used to purify the plasmid DNA, the final clone.

Cultures of competent INVαF' E. coli (Invitrogen Corporation, Carlsbad, Calif.) were transformed according to the manufacturers instructions. The transformed cultures were plated on LB plates comprising 100 µg/ml ampicillin and 1.6 mg X-Gal. White colonies were chosen, screened with PCR, and sequenced. The clone that comprised the DNA sequence of the final clone was chosen, grown overnight in a LB broth culture containing 100 μg/ml ampicillin. Plasmid purification was performed on the broth culture with the Qiagen Plasmid Mini Purification Kit (Qiagen, Carlsbad, Calif.). The plasmid DNA was resequenced for confirmation. This plasmid DNA was then used for the next mutation.

The mutated sequences were identical to the wild type sequences in length, base composition and location. Mutated sequences were chosen that had optimal primer characteristics without matching any known naturally occurring DNA sequences. The mutated sequences were checked with a nucleotide BLAST search to confirm the uniqueness of the sequences. See http://www.ncbi.nlm.nih.gov/BLAST/. The final product is the IPC nucleic acid molecule of the present invention, a cloned fragment of DNA having a unique sequence that can be used in any probe-based PCR assay with specific primers and probes. Additionally, the IPC nucleic acid molecule of the present invention may be used with fluorescence resonance energy transfer (FRET), Scorpions, and Molecular Beacons assays. See Szollosi, el al. (1998) Cytometry 34(4):159–179; Schweitzer and Kingsmore (2001) Curr. Opin. Biotechnol. 12(1):21–27; and Antony and Subramaniam (2001) J. Biomol. Struct. Dyn. 19(3):497–504, which are herein incorporated by reference.

The IPC nucleic acid molecule of the present invention may be used in a probe-based nucleic acid diagnostic assay to determine the presence or absence of PCR inhibitors. An assay utilizing the IPC nucleic acid molecule of the present invention can either be run by itself or multiplexed with any other diagnostic assay. The IPC nucleic acid molecule of the present invention may be used as a control assay to troubleshoot probe-based nucleic acid assay problems such as PCR assays. For example, the IPC nucleic acid molecule of the present invention may be used to determine if a problem relates to the reagents, operator technique, or instrumentation.

The IPC nucleic acid molecule of the present invention may be multiplexed or used in conjunction with other assays for the detection of an organism based on the presence of a target nucleic acid molecule that is unique to the organism. For example, the IPC nucleic acid molecule of the present invention may be used in conjunction with assays, known in the art, for organisms belonging to *Bacillus, Mycobacterium, Francisella, Brucella, Clostridium, Yersinia, Variola, Orthopox,* and *Burkholderia.* See e.g. Fasanella, A. et al. (2003) J. Clin. Microbiol. 41(2):896–899 (*Bacillus anthracis*); Drago, L. et al. (2002) J. Clin Microbiol. 40(11):4399 (*Bacillus anthracis*); Espy, M. J. et al. (2002) Mayo Clin. Proc. 77(7):624–628 (bioterrorism agents); Montenegro, S. H. et al. (2003) Clin. Infect. Dis. 36(1): 16–23 (*Mycobacterium tuberculosis*); Johansson, A. et al. (2000) J. Clin. Microbiol. 38(11):4180–4185 (*Francisella tularensis*); Emanuel, P. A. et al. (2003) J. Clin. Microbiol. 41(2):689–693 (*Francisella tularensis*); Navarro, E. et al. (2002) FEMS Immunol. Med. Microbiol. 34(2): 147–151 (*Brucella* spp); Bricker, B. J. (2002) Vet. Microbiol. 90(1–4):435–446 (*Brucella*); Lindstrom, M. et al. (2001) Appl. Environ. Microbiol. 67(12):5694–5699 (*Clostridium botulinum); Lindler, L. E. et al. (*2001) J. Clin. Microbiol. 39(10):3649–3655 (*Yersinia pestis*); Radnedge, L. et al. (2001) Appl. Environ. Microbiol. 67(8):3759–3762 (*Yersinia pestis*); Czerny, C. P. et al. (1997) Arch. Virol. Suppl. 13:13–24 (orthopox virus); Epsy, M. J. et al. (2002) J. Clin. Microbiol. 40(6):1985–1988 (smallpox); Meyer, H. et al. (2002).J. Vet. Med. B. Infect. Dis. Vet. Public Health 49(l):17–19 (*variola*); Meyer, H. et al. (1997) J. Virol. Methods 64(2):217–221 (orthopox); Woo, P. C. et al. (2002) Diagn. Microbiol. Infect. Dis. 44(2):143–149 (*Burkholderia*); and Vermis, K. et al. (2002) J. Med. Microbiol. 51(11):937–940 (*Burkholderia*), which are herein incorporated by reference.

As used herein, "nucleic acid molecule", "polynucleotide", and "oligonucleotide" are used interchangeably to refer DNA and RNA molecules of natural or synthetic origin which may be single-stranded or double-stranded, and represent the sense or antisense strand. The nucleic acid molecules of the present invention may contain known nucleotide analogs or modified backbone residues or linkages, and any substrate that can be incorporated into a polymer by DNA or RNA polymerase. Examples of such analogs inlude phospborothioates, phosphoramidates, methyl phosphonates, chiral-methyl phosphonates, 2-O-methyl ribonucleotides, peptide-nucleic acids (PNAs), and the like.

In preferred embodiments, the IPC nucleic acid molecule of the present invention is isolated. As used herein, "isolated" refers to a nucleic acid molecule that is isolated from its native environment. An "isolated" nucleic acid molecule may be substantially isolated or purified from the genomic DNA of the species from which the nucleic acid molecule was obtained. An "isolated" polynucleotide may include a nucleic acid molecule that is separated from other DNA segments with which the nucleic acid molecule is normally or natively associated with at either the 5' end, 3' end, or both.

The IPC nucleic acid molecule of the present invention may be in its native form or synthetically modified. The IPC nucleic acid molecule of the present invention may be single-stranded (coding or antisense) or double-stranded, and may be DNA (genomic, cDNA or synthetic) or RNA molecules. RNA molecules include mRNA molecules, which contain introns and correspond to a DNA molecule in a one-to-one manner, and mRNA molecules, which do not contain introns. The IPC nucleic acid molecule of the present invention may be linked to other nucleic acid molecules, support materials, reporter molecules, quencher molecules, or a combination thereof. Other nucleic acid molecules include promoters, polyadenylation signals, additional restriction enzyme sites, multiple cloning sites, other coding segments, and the like. It is therefore contemplated that a nucleic acid fragment of almost any length may be employed, with the total length preferably being limited by the ease of preparation and use in the intended recombinant DNA or PCR protocol. In some embodiments of the present invention, nucleic acid sequences comprising the IPC oligonucleotide described herein are contemplated.

The IPC nucleic acid molecule of the present invention may be readily prepared by conventional methods known in the art, for example, directly synthesizing the nucleic acid sequence using methods and equipment known in the art such as automated oligonucleotide synthesizers, PCR technology, recombinant DNA techniques, and the like.

The IPC nucleic acid molecule of the present invention may contain a label such as quencher molecule and a reporter molecule. A wide variety of labels and conjugation techniques are known by those skilled in the art and may be used in various nucleic acid and amino acid assays employing the IPC nucleic acid molecule of the present invention. As used herein a "label" or a "detectable moiety" is a composition that is detectable by spectroscopic, photochemical, biochemical, immunochemical, or chemical means. A "labeled" nucleic acid molecule comprises a bound label such that the presence of the nucleic acid molecule may be detected by detecting the presence of the label bound to thereto. The label may be bound to the nucleic acid molecule via a covalent bond, such as a chemical bond, or a noncovalent bond, such as ionic, van der Waals, electrostatic, or hydrogen bonds. Methods known in the art for producing labeled hybridization or PCR probes for detecting sequences related to polynucleotides may be used and include oligolabeling, nick translation, end-labeling or PCR amplification using a labeled nucleotide, and the like, preferably end-labeling. Suitable reporter molecules and quencher molecules that may be used include radionucleotides, enzymes, fluorescent, chemiluminescent, or chromogenic agents as well as substrates, cofactors, inhibitors, magnetic particles, and the like. In preferred embodiments, a fluorescent reporter molecule and quencher molecule are used.

As used herein, a "nucleic acid probe" and "probe" refers to a nucleic acid molecule that is capable of binding to a target nucleic acid molecule having a sequence that is complementary to the sequence of the nucleic acid probe. A probe may include natural or modified bases. See e.g. MPEP 2422, 8$^{th}$ ed., which is herein incorporated by reference. The nucleotide bases of the probe may be joined by a linkage other than a phosphodiester bond, so long as the linkage does not interfere with the ability of the nucleic acid molecule to bind a complementary nucleic acid molecule. The probe may bind a target sequence that is less than 100% complementary to the probe sequence and such binding depends upon the stringency of the hybridization conditions. The presence or absence of the probe may be detected to determine the presence or absence of a target sequence or subsequence in a sample. The probe may contain a label whose signal is detectable by methods known in the art. As used herein a "signal" is a measurable characteristic. Where the label is a reporter molecule and a quencher molecule, the signal may increase or decrease upon dissociation of reporter molecule and the quencher molecule. For example, if the reporter molecule is a fluorophore, separation of the quencher from the fluorophore will generate a detectable signal due to an increase in light energy emitted by the fluorophore in response to illumination.

As used herein, a "target" nucleic acid molecule may be any nucleic acid molecule, the presence and/or amount of which is desired to be known. In some embodiments, the sequence of the target nucleic acid molecule is known. In some embodiments, e.g., mutation detection, the sequence of the target nucleic acid molecule may be a sequence that is suspected of having alterations, i.e. differences, from a reference nucleic acid sequence. In these embodiments, the sequence of the target nucleic acid molecule may or may not be known, and the "reference nucleic acid sequence" is a known nucleic acid sequence to which the sequence of the target nucleic acid molecule may be compared. The alteration in the target nucleic acid molecule may be in a single nucleotide base or more than a single nucleotide base. Such an alteration may be a known polymorphic alteration, such as a single nucleotide polymorphism.

The present invention further provides kits for use with nucleic acid hybridization assays such as PCR amplification and PCR assays, including TaqMan® based assays, fluorescence resonance energy transfer (FRET), Scorpions, and Molecular Beacons assays. See Szollosi, et al. (1998) Cytometry 34(4):159–179; Schweitzer and Kingsmore (2001) Curr. Opin. Biotechnol. 12(1):21–27; and Antony and Subramaniam (2001) J. Biomol. Struct. Dyn. 19(3): 497–504, which are herein incorporated by reference. Such kits comprise the IPC nucleic acid molecule and one or more components necessary for performing the assay. Components may be compounds, reagents, containers, instructions and/or equipment.

The kits may be used for any one or more of the uses described herein, and, accordingly, may contain instructions for any one or more of the following uses: determining whether a target nucleic acid sequence is present in a sample, detecting a target nucleic acid sequence, quantifying a target nucleic acid sequence, comparing target nucleic acid sequence to a reference sequence, determining genotype, determining allele composition of a target nucleic acid, detecting and/or quantifying multiple nucleic acid sequences, and use of the methods in conjunction with nucleic acid amplification techniques.

The kits of the invention comprise one or more containers comprising any combination of the components or reagents described herein. For example, in one embodiment, the kit comprises the IPC nucleic acid molecule of the present invention and a set of primers and probes for conducting an assay for a target nucleic acid molecule. The kit may further include at least one label and at least one substrate or for producing a signal. The kit may further include deoxynucleoside triphosphates and/or ribonucleoside triphosphates. The kit may further include one or more suitable buffers for conducting the given assay. Each component of the kit can be packaged in separate containers or some components can be combined in one container where cross-reactivity and shelf life permit.

The kits of the invention may optionally include a set of instructions, generally written instructions, although electronic storage media (e.g., magnetic diskette or optical disk) containing instructions are also acceptable, relating to the use of components of the methods of the present invention for the intended nucleic acid detection and/or quantification, and/or, as appropriate, for using the detection and quantification methods in conjunction with amplification techniques. The instructions included with the kit generally include information as to reagents (whether included or not in the kit) necessary for practicing the methods of the presentation invention, instructions on how to use the kit, and/or appropriate reaction conditions.

As used herein, "sequence identity" in the context of two or more nucleic acid molecules, refers to two or more sequences or subsequences that are the same or have a specified percentage of nucleotide bases that are the same (i.e., 70% identity, optionally 75%, 80%, 85%, 90%, or 95% identity over a specified region), when compared and aligned for maximum correspondence over a comparison window, or designated region as measured using one of the following sequence comparison algorithms or by manual alignment and visual inspection. The percentage of sequence identity may be calculated by comparing two optimally aligned sequences over the window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity.

Methods of alignment of sequences for comparison are well-known in the art. See e.g. Smith & Waterman (1981) Adv. Appl. Math. 2:482; Needleman & Wunsch (1970) J. Mol. Biol. 48:443; and Pearson & Lipman (1988) PNAS USA 85:2444, which are herein incorporated by reference. Alignment may be conducted using computer programs such as GAP, BESTFIT, FASTA, and TFASTA in the Wisconsin Genetics Software Package (Genetics Computer Group, 575 Science Dr., Madison, Wis.), or manually by visual inspection. See also Feng & Doolittle (1987) J. Mol. Evol. 35:351–360; Higgins & Sharp (1989) CABIOS 5:151–153; and Devereaux et al. (1984) Nuc. Acids Res. 12:387–395, which are herein incorporated by reference.

Alternatively, BLAST and BLAST 2.0 algorithms may be used to determine the sequence identity of two or more sequences. See Altschul et al. (1977) Nuc. Acids Res. 25:3389–3402 and Altschul et al. (1990) J. Mol. Biol. 215:403–410, which are herein incorporated by reference. BLAST analyses are publicly available through the National Center for Biotechnology Information at http://www.ncbi.nlm.nih.gov/.

As provided herein, the IPC nucleic acid molecules of the present invention include nucleic acid molecules that have at least about 70% identity, preferably about 80% identity or more, more preferably about 90% identity or more, more preferably about 95% identity or more, over the 548 bp region set forth in SEQ ID NO: 49. Nucleic acid molecules that have sequences that have at least about 70% identity to SEQ ID NO: 49 are "substantially identical" to SEQ ID NO: 49.

As used herein, the phrase "selectively (or specifically) hybridizes to" refers to the binding, duplexing, or hybridizing of a nucleic acid molecule to a particular nucleotide sequence only in a sample comprising other nucleic acid molecules under stringent hybridization to moderate hybridization conditions. For selective or specific hybridization, a positive signal is at least about 2 times, preferably about 5 times, more preferably about 10 times the background hybridization. Stringent hybridization conditions are about 5° C. below the thermal melting temperature (Tm) of the probe to about 10° C. below Tm. Moderate hybridization conditions are about 10° C. below the thermal melting temperature (Tm) of the probe to about 20° C. to about 25° C. below Tm.

The following examples are intended to illustrate but not to limit the invention.

EXAMPLE 1

Mutagenic Process

Figure 2:
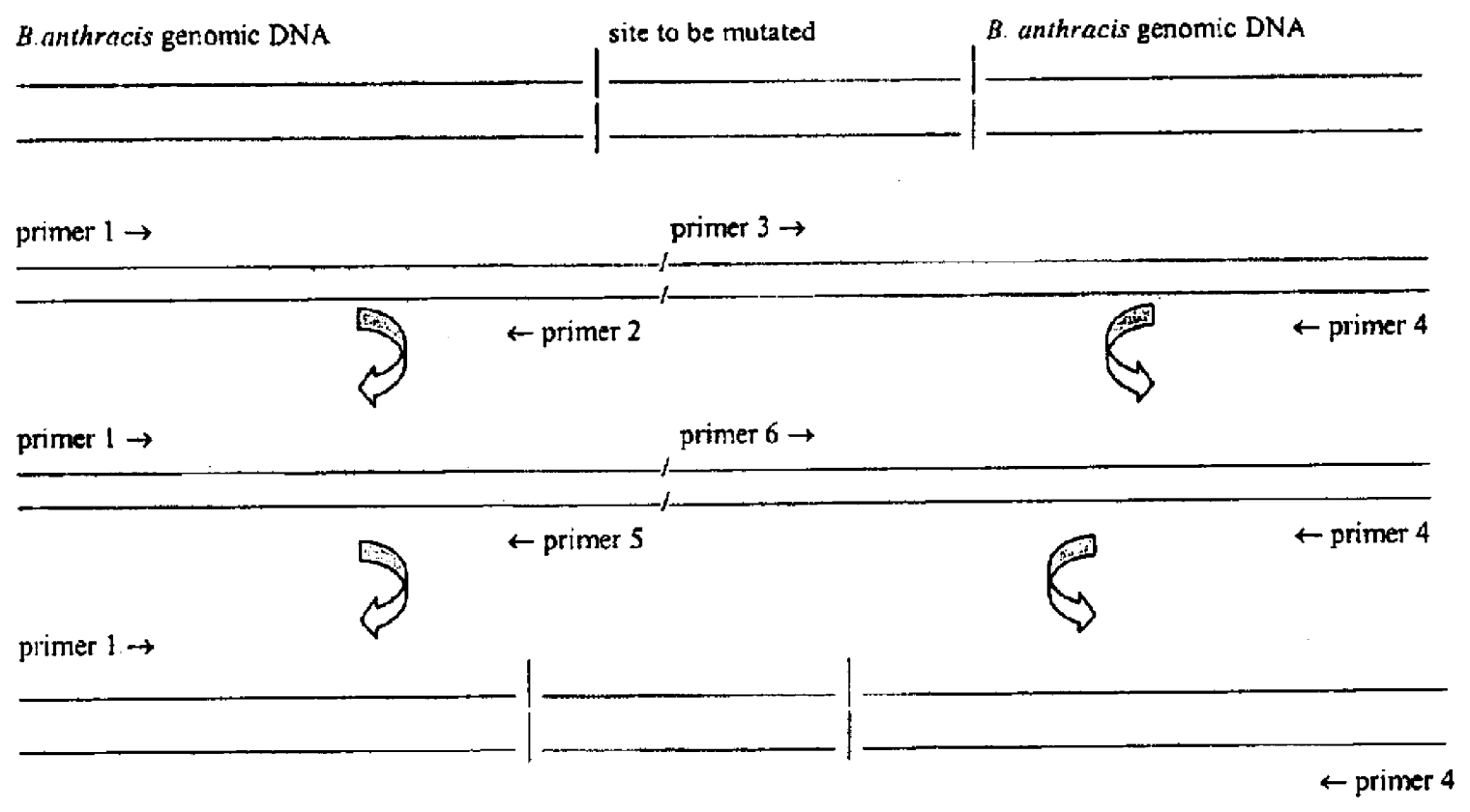

FIG. 2 schematically shows the site-directed mutagenesis process used to generate the IPC nucleic acid molecule of the present invention. As shown, the first two sets of PCR reactions allowed ½ of the mutated sequence to be incorporated into the generated PCR fragments. Template DNA was placed in one reaction with primers 1 and 2, and another reaction with primers 3 and 4. The next two sets of PCR reactions allowed for full incorporation of the mutated sequence into the PCR products. In one reaction, the primer set 1 and 2 generated DNA fragment was used as a template for amplification with primers 1 and 5. The other reaction used the primer set 3 and 4 generated DNA fragment as a template for amplification with primers 4 and 6. In the final round, both fragments from primers 1 and 5 and from primers 4 and 6 were used as primers for each other in an overlap extension reaction. Partway through the PCR, primers 1 and 4 were added to the reaction. The final product was one DNA fragment that fully incorporated the mutated sequence.

After completing the mutagenesis of all three sites, the sequence was verified. Clone 1, the final clone chosen, was re-sequenced. Both, the forward strand and the reverse strand in duplicate with the dideoxy sequencing method using the Big Dye Sequencing Kit (Applied Biosystems, Foster City, Calif.).

EXAMPLE 2

Effect of Inhibitors on IPC

The effect of three inhibitors, hemoglobin, heparin, and EDTA, on the IPC nucleic acid molecule of the present invention was tested. The IPC DNA was titrated to use the smallest amount possible to still obtain consistent results, yet make the assay very sensitive to inhibition. Using the Smart Cycler® (Cepheid, Sunnyvale, Calif.) 1 fg of IPC DNA was found to be optimal for the methods herein. The reagents used were Idaho Technology PCR Reagents (Idaho Technology, Idaho Falls, Id.), which include the 10×buffer with 30 mM $MgCl_2$ and 10×dNTP. 5×SC buffer, an additive recommended by Cepheid (Cepheid, Sunnyvale, Calif.), the manufacturers of the Smart Cycler®, and Platinum Taq DNA Polymerase (Invitrogen, Carlsbad, Calif.), was also used. The PCR was started with a 2-minute activation at 95° C. and then 45 cycles of 95° C. for 1 second and 65° C. for 20 seconds. The assay was tested against these three inhibitors using probes labeled with two different reporter dyes, FAM and ROX. The quencher on both of these probes was TAMRA. Biosearch Technologies, Novato, Calif., manufactured the probes.

A. Hemoglobin

The effect of hemoglobin was initially tested with a 10-fold dilution series from 6 µg/µL to 0.0006 µg/µL final concentration in a 25 µl reaction volume and then tested with 2-fold dilution series from 0.06 µg/µL to 0.0006 µg/µL final concentration.

With both reporter dyes, FAM and ROX, 0.06 µg/µL was partially inhibitory. Inhibition was completely relieved at 0.03 µg/µL.

B. Heparin

The effect of heparin was initially tested with 10-fold dilution series from 2 Units/µL to 0.00002 Units/µL final concentration in a 25 µl reaction volume and then 0.002 Units/µL to 0.00025 Units/µL final concentration.

Heparin was completely inhibitory at 0.0005 Units/µL and inhibition was completely relieved at 0.00025 Units/µL.

C. EDTA

The effect of EDTA was tested with 2-fold dilution series from 5 mM to 0.156 mM final concentration in a 25 µl reaction.

EDTA was completely inhibitory at 5 mM and 2.5 mM. With the FAM probe, inhibition was completely relieved at 1.25 mM. With the ROX probe, 1.25 mM was partially inhibitory and inhibition was not completely relieved until 0.625 mM.

EXAMPLE 3

Limit of Detection

To determine whether the IPC nucleic acid molecule of the present invention affects the limit of detection of a given assay, the following was conducted.

The IPC nucleic acid molecule was duplexed with all of the assays that we currently use on the Smart Cycler®. The IPC IPC nucleic acid molecule was labeled with ROX and the primary assay probes were labeled with FAM. Ten-fold serial dilutions were performed on all genomic DNA samples for the primary assays. The limit of detection was tested in triplicate for each assay.

A. Assay for *Bacillus anthracis*

The primer set used was BAPA3U/5L and the probe was BAPA3P2A.

```
BAPA3U:
5' TTCAAGTTGTACTGGACCGATTCTC 3'        (SEQ ID NO:50)

BAPA5L:
5' TCCATCATTGTCACGGTCTGG 3'            (SEQ ID NO:51)

BAPA3P2A:
5' CCGTAGGTCCAGCACTTGTACTTCGCTT 3'     (SEQ ID NO:52)
```

The reaction mix included 10×PCR buffer with 5 mM $MgCl_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 65° C. for 20 seconds. Testing was performed with and without the IPC assay. One fg of IPC DNA was used. Limit of detection of the PA assay was 10 fg in both cases.

B. Assay for *Bacillus anthracis*

The primer set used was BACAPBU2/L2 and the probe was BACAPBP2.

```
BACAPBU2:
5' GCTGACCAATCTAAGCCTGC 3'             (SEQ ID NO:53)

BACAPBL2:
5' GGCAAAACATCCCTAGCAAA 3'             (SEQ ID NO:54)

BACAPBP2:
5' TTGTAATTATGAATTGCCGCCCTGACC 3'      (SEQ ID NO:55)
```

The reaction mix included 10×PCR buffer with 5 mM $MgCl_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 65° C. for 20 seconds. Testing was performed with and without the IPC assay. Five fg of IPC DNA were used. Limit of detection of the PA assay was 100 fg without IPC and 1 pg with IPC.

C. Assay for *Brucella*

The primer set used was BROMPF394/R474 and the probe was BROMP25-420S.

```
BROMPF394:
5' AACAAGGCCAAGACCAGCACC 3'            (SEQ ID NO:56)

BROMPR474:
5' CTGGAAGTTCCAGCCAGCAA 3'             (SEQ ID NO:57)

BROMP25-420S:
5' CAGCATCAAGCCTGACGATTGGAAGG 3'       (SEQ ID NO:58)
```

The reaction mix included 10×PCR buffer with 5 mM $MgCl_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection of the PA assay was 1 fg for both. Without IPC there was 1 hit out of 3 for 100 ag.

D. Assay for *Clostridium botulinum*

The primer set used was CBOTA4U/4L and the probe was CBOTA4P2A.

```
CBOTA4U:
5' GATATAGGCTTTATAGGATTTCATCAG 3'      (SEQ ID NO:59)

CBOTA4L:
5' CCTTTCTCCCCATCCATC 3'               (SEQ ID NO:60)

CBOTA4P2A:
5' TCCCATGAGCAACCCAAAGTCCTACT 3'       (SEQ ID NO:61)
```

The reaction mix included 10×PCR buffer with 4 mM $MgCl_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection of the PA assay was 100 fg for both. Without IPC there was 1 hit out of 3 for 10 fg.

E. Assay for *Yersinia pestis*

The primer set used was YPPLA3U/3L and the probe was YPPLAP3F.

```
YPPLA3U:
5' GGTACCGTAATTAACGCTGG 3'             (SEQ ID NO:62)

YPPLA3L:
5' GTCTGAGTACCTCCTTTGCC 3'             (SEQ ID NO:63)

YPPLAP3F:
5' ACCTAATGCCAAAGTCTTTGCGGA 3'         (SEQ ID NO:64)
```

The reaction mix included 10×PCR buffer with 4 mM $MgCl_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection with (2 out of 3) and without (2 out of 3) IPC was 1 fg

F. Assay for *Bacillus anthracis*

The primer set used was BACAPB4U/4L and the probe was BACAPBP1S.

```
BACAPB4U:
5' CAGATAATGCATCGCTTGCTTTAG 3'         (SEQ ID NO:65)

BACAPB4L:
5' GGATGAGCATTCAACATACCACG 3'          (SEQ ID NO:66)

BACAPBP1S:
5' CAGAGGCTCTTGGGATTGATGAGGAAACA 3'    (SEQ ID NO:67)
```

The reaction mix included 10×PCR buffer with 5 mM $MgCl_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 65° C. for 20 seconds. Testing was performed with and without the IPC assay. One fg of IPC DNA was used. Limit of detection with IPC was 100 fg and without IPC was 10 fg (2 out of 3)

G. Assay for *Bacillus anthracis*

The primer set used was BAVRRA3U/3L and the probe was BAVRRA3P1S.

```
BAVRRA3U:
5' AAATGTATGAATCAAACGAAACGC 3'      (SEQ ID NO:68)

BAVRRA3L:
5' CAGGGCTTACAGATTGAACG 3'          (SEQ ID NO:69)

BAVRRA3P1S:
5' CGGTGCAGCAACTACAGCAGCA 3'        (SEQ ID NO:70)
```

The reaction mix included 10×PCR buffer with 3 mM $MgCl_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection with and without IPC was 10 fg.

H. Assay for *Francisella tularensis*

The primer set used was FTTULU1/L1 and the probe was FTTULP1F.

```
FTTULU1:
5' CAGCATACAATAATAACCCACAAGG 3'     (SEQ ID NO:71)

FTTULL1:
5' TCAGCATACTTAGTAATTGGGAAGC 3'     (SEQ ID NO:72)

FTTULP1F:
5' TTACAATGGCAGGCTCCAGAAGGTTC 3'    (SEQ ID NO:73)
```

The reaction mix included 10×PCR buffer with 5 mM $MgCl_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 55° C. for 20 seconds. Testing was performed with and without the IPC assay. One fg of IPC DNA was used. Limit of detection with IPC was 10 fg (2 out of 3) and without IPC was 1 fg.

I. Assay for *Yersinia pestis*

The primer set used was YPPIMU1/L1 and the probe was YPPIMP1R.

```
YPPIMU1:
5' AGTGGCCTTGCAGAAAAAA 3'           (SEQ ID NO:74)

YPPIML1:
5' GTAAACTCGGTTTGCTTGAAG 3'         (SEQ ID NO:75)

YPPIMP1R:
5'-TGTCTGTTTCCCATAGATGCCATGA 3'     (SEQ ID NO:76)
```

The reaction mix included 10×PCR buffer with 5 mM $MgCl_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection with (3 out of 3) and without IPC (1 out of 3) was 1 fg.

J. Assay for *Orthopox sp.*

The primer set used was OPSPF89/R219 and the probe was Op-p143S.

```
OPSPF89:
5' GATGATGCAACTCTATCATGTA 3'        (SEQ ID NO:77)

OPSR219:
5' GTATAATTATCAAAATACAAGACGTC 3'    (SEQ ID NO:78)

Op-p143S:
5' AGTGCTTGGTATAAGGAG 3'            (SEQ ID NO:79)
```

The reaction mix included 10×PCR buffer with 5 mM $MgCl_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection with and without IPC was 100 fg.

K. Assay for *Francisella tularensis*

The primer set used was FOPAF708/R846 and the probe was FtFOPA765S.

```
FOPAF708:
5' CTGGTTTAACATGGTTCTTTGGTG 3'      (SEQ ID NO:80)

FOPAR846:
5' CCAGCAGGTAAAACATACTTAGACTCA 3'   (SEQ ID NO:81)

FtFOPA765S:
5' TCCAGGATAATGGTGCGACTACAGCTGC 3'  (SEQ ID NO:82)
```

The reaction mix included 10×PCR buffer with 5 mM $MgCl_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection with and without IPC was 10 fg.

L. Assay for *Variola*

The primer set used was J7R3U/3L and the probe was VARJ7R3p.

```
J7R3U:
5' CATCATTGGCGGTTGATTTA 3'          (SEQ ID NO:83)

J7R3L:
5' TCATCTGGAGAATCCACAACA 3'         (SEQ ID NO:84)

VARJ7R3p:
5' CAAGACGTCGGGACCAATTACTAATA 3'    (SEQ ID NO:85)
```

The reaction mix included 10×PCR buffer with 5 mM $MgCl_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection with (2 out of 3) and without (3 out of 3) IPC was 100 ag.

M. Assay for *Burkholderia*

The primer set used was BPISO2F1/R1 and the probe was BMIS02PF3.

```
BPISO2F1:
5' CTCGAGGTGGAGAATGCCC 3'          (SEQ ID NO:86)

BPISO2R1:
5' CGCTCGGAGATGTTGACCTTC 3'        (SEQ ID NO:87)

BMISO2PF3:
5' TGGCCGAAGCAATGCTCGATATGG 3'     (SEQ ID NO:88)
```

The reaction mix included 10×PCR buffer with 5 mM $MgCl_2$ (Idaho Technologies, Idaho Falls, Id.), 5×SCAR additive (Cepheid, Sunnyvale, Calif.), and Platinum Taq DNA Polymerase (Invitrogen Corporation, Carlsbad, Calif.). Thermal cycling was performed on the Cepheid Smart Cycler® under the following conditions: 95° C. for 2 minutes and then 45 cycles of 95° C. for 1 second and 60° C. for 20 seconds. Testing was performed with and without the IPC assay. One fg of IPC DNA was used. Limit of detection without IPC was 10 ag. This assay did not work in the presence of the IPC.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

---

We claim:

1. An isolated nucleic acid molecule comprising the sequence set forth in SEQ ID NO:49.

2. The isolated nucleic acid molecule of claim 1, wherein the nucleic acid molecule consists essentially of the sequence set forth in SEQ ID NO:49.

3. The isolated nucleic acid molecule of claim 1, wherein the nucleic acid molecule consists of the sequence set forth in SEQ ID NO:49.

4. A probe comprising the isolated nucleic acid molecule of claim 1 and a label.

5. A probe comprising the isolated nucleic acid molecule of claim 1, a reporter molecule, and a quencher molecule.

6. The probe of claim 5, wherein the reporter molecule produces a signal upon the separation of the reporter molecule and the quencher molecule.

7. The probe of claim 5, wherein the quencher molecule is capable of quenching the signal of the reporter molecule.

8. The probe of claim 7, wherein the reporter molecule is a fluorophore.

9. The probe of claim 8, wherein the fhiorophore is FAM, ROX, Texas Red, TET, TAMRA, JOE, HEX, CAL Red, or VIC.

10. The probe of claim 5, wherein the probe is capable of being cleaved by a protein thereby separating the reporter molecule from the quencher molecule.

11. The probe of claim 10, wherein the protein is Taq polymerase.

12. An assay comprising contacting the probe of claim 4 with a target nucleic acid molecule and detecting the presence or measuring the amount of the target nucleic acid.

13. The assay of claim 12, wherein the assay is a nucleic acid hybridization assay.

14. The assay of claim 12, wherein the assay is a TaqMan® based assay.

15. The assay of claim 12, further comprising conducting PCR amplification.

16. The assay of claim 15, further comprising detecting the presence or measuring the amount of the probe.

17. The assay of claim 16, wherein the absence of the target nucleic acid molecule and the absence of the probe indicate a true negative result for the target nucleic acid molecule.

18. The assay of claim 16, wherein the absence of the target nucleic acid molecule and the presence of the probe indicate a false negative result for the target nucleic acid molecule.

19. A kit for a probe-based nucleic acid assay comprising the isolated nucleic acid molecule of claim 1 packaged with instructions for use.

20. The kit of claim 19, wherein the isolated nucleic acid molecule contains a label.

21. The kit of claim 20, wherein the label is a reporter molecule and a quencher molecule.

22. The kit of claim 19, wherein the probe-based nucleic acid assay is for the detection of an organism.

23. The kit of claim 22, wherein the organism belongs to *Bacillus, Mycobacterium, Francisella, Brucella, Clostridium, Yersinia, Variola, Orthopox, or Burkholderia.*

24. The kit of claim 22, further comprising reagents or components for detecting the presence of a nucleic acid molecule belonging to the organism.

25. A probe which comprises the isolated nucleic acid of claim 1.

26. An assay which comprises contacting the probe of claim 25 with a target nucleic acid molecule.

27. A kit for a probe-based nucleic acid assay comprising the isolated nucleic acid molecule of claim 1 packaged with instructions for use.

* * * * *